United States Patent
Chen et al.

(10) Patent No.: US 11,409,999 B2
(45) Date of Patent: Aug. 9, 2022

(54) METHOD OF LABELLING FEATURES FOR IMAGE RECOGNITION AND APPARATUS THEREOF

(71) Applicant: Industrial Technology Research Institute, Hsinchu (TW)

(72) Inventors: Guan-An Chen, Hsinchu (TW); Jian-Ren Chen, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 28 days.

(21) Appl. No.: 16/921,896

(22) Filed: Jul. 6, 2020

(65) Prior Publication Data

US 2021/0326637 A1    Oct. 21, 2021

(30) Foreign Application Priority Data

Apr. 21, 2020  (TW) .................. 109113231

(51) Int. Cl.
*G06V 10/40*    (2022.01)
*G06K 9/62*    (2022.01)
(Continued)

(52) U.S. Cl.
CPC .......... *G06K 9/628* (2013.01); *G06K 9/6256* (2013.01); *G06N 3/02* (2013.01); *G06T 7/73* (2017.01);
(Continued)

(58) Field of Classification Search
CPC ........ G06K 9/46; G06K 9/6256; G06K 9/628; G06N 3/02; G06T 2207/20084; G06T 7/73
See application file for complete search history.

(56) References Cited

U.S. PATENT DOCUMENTS 10,395,772 B1    8/2019 Lucas et al.
2017/0135577 A1    5/2017 Komogortsev
(Continued)

FOREIGN PATENT DOCUMENTS

CN    107358606    11/2017
CN    108427957    8/2018
(Continued)

OTHER PUBLICATIONS

Bolei Zhou, et al., "Learning Deep Features for Discriminative Localization", The IEEE Conference on Computer Vision and Pattern Recognition (CVPR), Jun. 27-30, 2016, pp. 2921-2929.
(Continued)

*Primary Examiner* — Ian L Lemieux
(74) *Attorney, Agent, or Firm* — JCIPRNET

(57) ABSTRACT

A method of labelling features for image recognition and an apparatus thereof are provided. The method includes inputting an image to be recognized to an image recognition model to obtain a classification result; obtaining a plurality of recognized features and positions of the recognized features from the image to be recognized based on activation maps respectively corresponding to a plurality of preset features in the classification result; and labelling the recognized features and the positions of the recognized features activating the classification result. Accordingly, the features determined by the image recognition model can be showed clearly by the method of labelling features for image recognition and the apparatus thereof.

12 Claims, 8 Drawing Sheets

(51) Int. Cl.
    *G06T 7/73*     (2017.01)
    *G06N 3/02*     (2006.01)
(52) U.S. Cl.
    CPC .... *G06V 10/40* (2022.01); *G06T 2207/20084* (2013.01)

(56) References Cited

U.S. PATENT DOCUMENTS

| | | | |
|---|---|---|---|
| 2018/0125446 A1* | 5/2018 | Boroczky | A61B 10/0241 |
| 2018/0144209 A1* | 5/2018 | Kim | G16H 30/40 |
| 2019/0325605 A1* | 10/2019 | Ye | G06V 10/32 |
| 2020/0069275 A1 | 3/2020 | Stavros | |
| 2020/0085290 A1* | 3/2020 | Wang | G06T 7/0014 |
| 2020/0178840 A1* | 6/2020 | Yeh | G06N 20/00 |
| 2020/0356842 A1* | 11/2020 | Guo | G06F 17/15 |
| 2021/0272681 A1* | 9/2021 | Zheng | G16H 30/40 |

FOREIGN PATENT DOCUMENTS

| | | |
|---|---|---|
| CN | 105718952 | 10/2018 |
| CN | 110070933 | 7/2019 |
| TW | I442326 | 6/2014 |
| TW | I617993 | 3/2018 |
| TW | 201923091 | 6/2019 |
| TW | 201942868 | 11/2019 |
| WO | 2016193025 | 12/2016 |

OTHER PUBLICATIONS

"Office Action of Taiwan Counterpart Application", dated Nov. 25, 2020, p. 1-p. 5.

* cited by examiner

| Class/Feature | F1 | F2 | F3 | F4 |
|---|---|---|---|---|
| C1 | ✓ | | | |
| C2 | ✓ | ✓ | | |
| C3 | ✓ | ✓ | ✓ | |
| C4 | ✓ | ✓ | ✓ | ✓ |

FIG. 4

METHOD OF LABELLING FEATURES FOR IMAGE RECOGNITION AND APPARATUS THEREOF

CROSS-REFERENCE TO RELATED APPLICATION

This application claims the priority benefit of Taiwan application no. 109113231, filed on Apr. 21, 2020. The entirety of the above-mentioned patent application is hereby incorporated by reference herein and made a part of this specification.

TECHNICAL FIELD

The disclosure relates to a method of labelling features for image recognition and an apparatus thereof.

BACKGROUND

With the advancement of technology, artificial Intelligence has been widely used in image recognition. However, these artificial intelligence image recognition technologies using machine learning and deep learning are like black boxes. Users often only learn of recognition results from a recognition system without knowing on which features in an image is the recognition system based.

In general, the artificial intelligence image recognition technologies are based on a maximum classification probability of a recognized image as a classification result. Taking an image classification of cats and dogs as an example, if 1% of the features in the image match "cat" features known by the recognition system and 99% of the features match "dog" features known by the recognition system, the recognition system will determine that the image contains dog.

However, in some situations that require accurate determination, if the maximum classification probability is simply used as a determination criterion, key information may be overlooked and users may have doubts about a determination result. For example, in the case where artificial intelligence is used in an interpretation training of a diabetic fundus image, since each severity of a diabetic lesion only shows a similarity to the feature, doctors cannot directly learn of a relationship between the determination result and its determination basis. In particular, when probability values for determining the classification are not much different from one another, relevant feature information between severity classes will be needed to facilitate doctors in further confirmation. Therefore, in terms of image recognition results, how to label the features corresponding to the determination result is an issue to be addressed by persons skilled in the art.

SUMMARY

The disclosure provides a method of labelling features for image recognition and an apparatus thereof, which can effectively label features on which an artificial intelligence image recognition result is based.

According to an embodiment of the disclosure, a method of labelling features for image recognition is provided, and includes inputting an image to be recognized to a neural network image recognition model to obtain a classification result. The neural network image recognition model classifies the image to be recognized to one of a plurality of classes. The classes are created based on a plurality of preset features. The classification result includes a plurality of activation maps respectively corresponding to the classes. The method further includes obtaining a plurality of recognized features activating the classification result and positions of the recognized features from the image to be recognized based on the activation maps respectively corresponding to the classes. The recognized features are separately corresponding to one of the preset features. The method further includes labelling the recognized features and the positions of the recognized features activating the classification result.

According to an embodiment of the disclosure, an apparatus of labelling features for image recognition is provided, and includes a central processing unit, a storage device and an input/output device. The central processing unit is configured to input an image to be recognized to a neural network image recognition model to obtain a classification result. The neural network image recognition model classifies the image to be recognized to one of a plurality of classes. The classes are created based on a plurality of preset features. The classification result includes a plurality of activation maps respectively corresponding to the classes. The storage device is coupled to the operation logic processing circuit, and configured to store the neural network image recognition model and the classification result. The input/output device is coupled to the central processing unit. The central processing unit is further configured to obtain a plurality of recognized features activating the classification result and positions of the recognized features from the image to be recognized based on the activation maps respectively corresponding to the classes. The recognized features are separately corresponding to one of the preset features. The input/output device is configured to display the recognized features activating the classification result and the positions of the recognized features.

Based on the above, the method and the apparatus of labelling features in the exemplary embodiment of the disclosure can extract the recognized features in the image based on the relationship between the features and the classes.

BRIEF DESCRIPTION OF THE DRAWINGS

FIG. 4 is a diagram illustrating a relationship between diabetic lesion severity classes and preset features.

DETAILED DESCRIPTION

Figure 1:
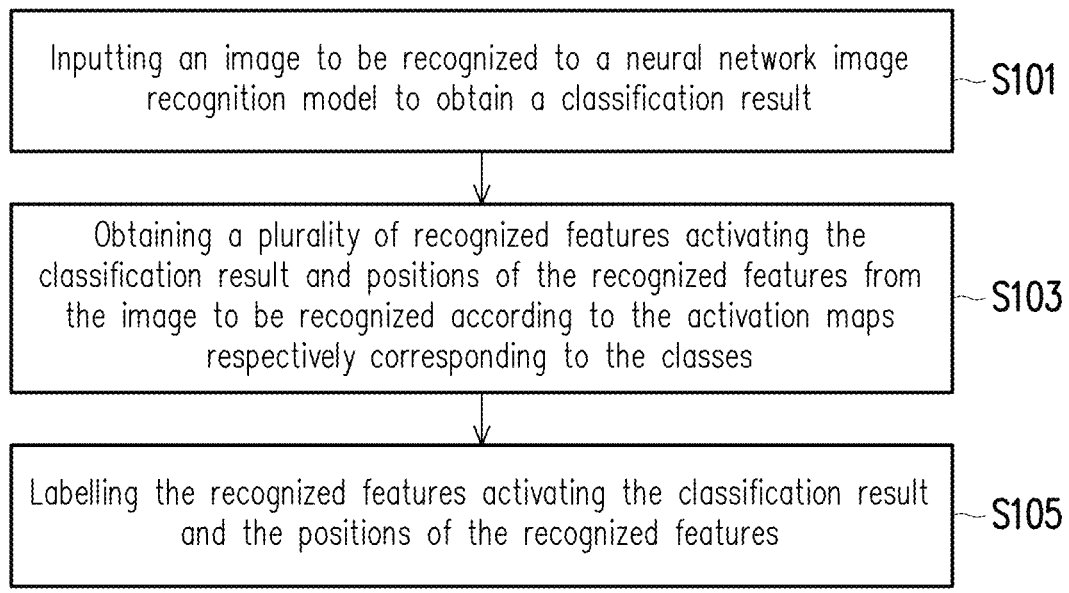
FIG. 1 is a flowchart of a method of labelling features for image recognition illustrated according to an exemplary embodiment of the disclosure.

The disclosure proposes a method of labelling features for image recognition, which can label features activating a recognition result of a neural network image recognition model created based on a plurality of classes from the recognition result. The method includes inputting an image to be recognized to the neural network image recognition model to obtain a classification result (step S101). Here, the neural network image recognition model classifies the image to be recognized to one of a plurality of classes, and the classification result includes a plurality of activation maps respectively corresponding to the classes. The method further includes obtaining a plurality of recognized features activating the classification result and positions of the recognized features from the image to be recognized based on the activation maps respectively corresponding to the classes (step S103); and labelling the recognized features activating the classification result and the positions of the recognized features (step S105). Accordingly, the relevant features and their positions can be displayed on the image to be recognized to help a user to confirm the features corresponding to the classification result and other possible hidden features.

In order to understand the disclosure in more detail, the diabetic fundus image recognition is taken below as an exemplary embodiment for description.

In general, based on severity, a diabetic lesion can be divided into four levels. (First level) Vessels on the retina show lesions, tumor damage start from the microvessels on the vein side, and blood leakage begins. The feature here is similar to capillary hemangioma. (Second level) In addition to the microvessels, hard exudate and retinal hemorrhage also appear. (Third level) Further damage to the retina, reduced local retina perfusion, ischemia and even closure of the entire capillary plexus. The feature here includes cotton-like spots or soft exudation, and intraretinal microvascular abnormality. (Fourth level) The feature here mainly includes neovascularization, which can be divided into two types: on the optic nerve or on other retina regions. Once the vitreous body is pulled, it is easy to produce larger vitreous hemorrhage and weaken vision. Symptoms of vitreous hemorrhage may be only a slight blur or red spots or black shadows in the form of spider webs in front of the eyes, or there can also be extreme vision loss. Based on the above, the presence or absence of the diabetic lesion and the level of the diabetic lesion are usually identified based on there are the presence or absence of microvascular abnormality, intraretinal hemorrhage, venous beading, intraretinal microvascular abnormality, neovascularization, and vitreous hemorrhage in the image. Among them, if none of the features is present, it means that the diabetic lesion does not exist (a zeroth level C0); if only microvascular abnormalities is present, the diabetic lesion is determined to be at a first level C1; if microvascular abnormality, intraretinal hemorrhage and venous beading are present, the diabetic lesion is determined to be at a second level C2; if microvascular abnormality (hereinafter referred to as the first preset feature), intraretinal hemorrhage and venous beading (hereinafter referred to as the second preset feature) and intraretinal microvascular abnormality (hereinafter referred to as the third preset feature) are present, the diabetic lesion is determined to be at a third level C3; if neovascularization and vitreous hemorrhage (hereinafter referred to as the fourth preset feature) are present, the diabetic lesion is determined to be at a fourth level C4.

Accordingly, the method of labeling features for image recognition of the disclosure will be described below with reference to a deep learning neural network image recognition model that can recognize whether the diabetic fundus image is the zeroth level C0, the first level C1, the second level C2, the third level C3 or the fourth level C4 of the diabetic lesion.

Figure 2:
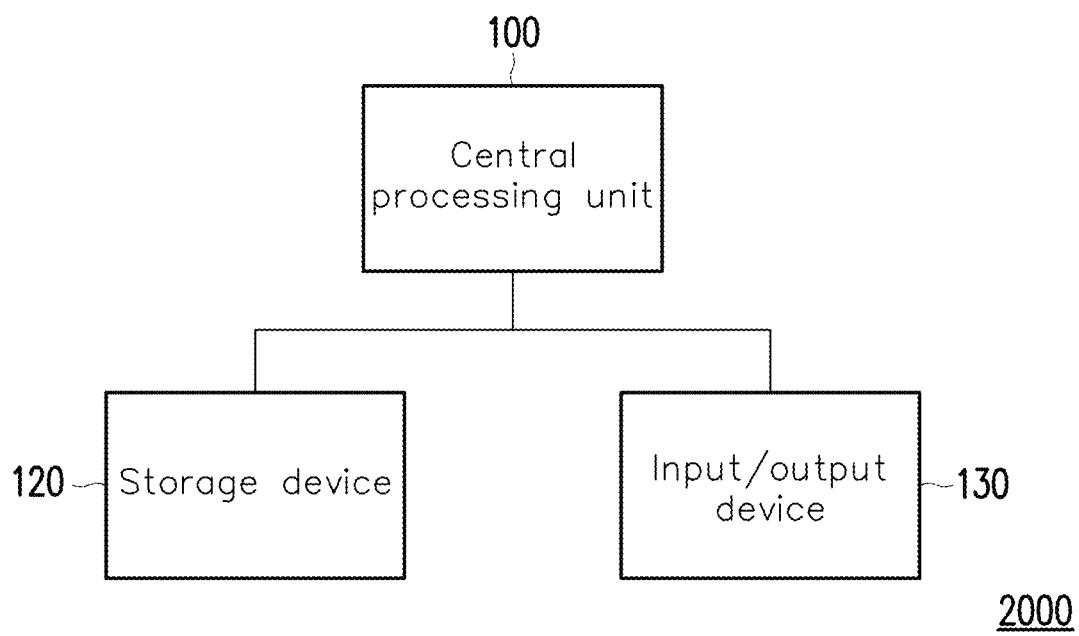
FIG. 2 is a block diagram of an apparatus of labelling features for image recognition illustrated according to an exemplary embodiment of the disclosure.

FIG. 2 is a block diagram of an apparatus of labelling features for image recognition illustrated according to an exemplary embodiment of the disclosure.

Referring to FIG. 2, an apparatus 2000 of labelling features for image recognition includes a central processing unit 100, a storage device 120 and an input/output device 130. The storage device 120 and the input/output device 130 are coupled to the central processing unit 100. The apparatus 2000 of labelling features for image recognition is, for example, a mobile device, a personal digital assistant (PDA), a notebook computer, a tablet computer, a general desktop computer or other electronic device, which is not limited herein.

The central processing unit 100 may be, for example, a processor for general purposes, a processor for special purposes, a conventional processor, a data signal processor, a plurality of microprocessors, one or more microprocessors, controllers, microcontrollers and Application Specific Integrated Circuit (ASIC) which are combined to a core of the digital signal processor, a Field Programmable Gate Array (FPGA), any other integrated circuits, a state machine, a processor based on Advanced RISC Machine (ARM) and similar products.

The storage device 120 may be, for example, any fixed or movable device including a RAM (Random Access Memory), a ROM (Read-Only Memory), a flash memory, a hard drive or other similar devices, or a combination of the above-mentioned devices. In this exemplary embodiment, the storage device 120 is stored with a neural network image recognition model for recognizing the diabetic fundus image. In this exemplary embodiment, the storage device 120 is further stored with programs like an operation logic processing module, a control module, etc., which may be executed by the central processing unit 100 to perform the method of labelling features for image recognition described in this exemplary embodiment.

The input/output device 130 is, for example, a device or an element configured to receive an input signal or an output signal of the user. For example, the input/output device 130 may include, for example, an image sensing element for capturing images, a device for inputting commands (e.g., keyboard, mouse, etc.), a display for displaying images and the like. For example, the user can use the input/output device 130 to input a plurality of training images respectively belonging to different diabetic lesion severity levels (i.e., the zeroth level C0, the first level C1, the second level C2, the third level C3 and the fourth level C4 of the diabetic lesion described above), so as to train the neural network image recognition model. The trained neural network image recognition model can be used to recognize and classify the diabetic fundus image.

Figure 3:
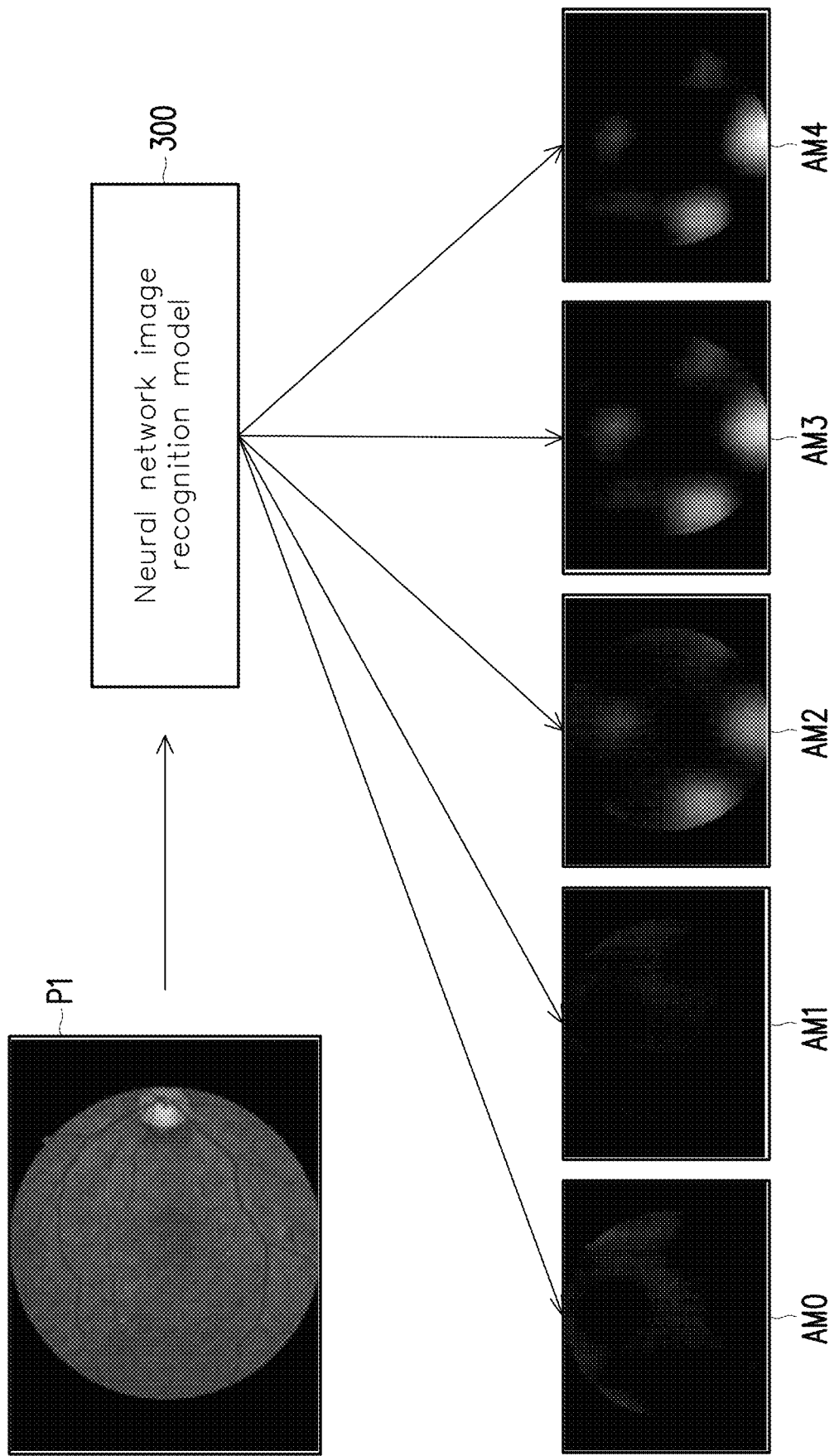
FIG. 3 is a schematic diagram of a diabetic fundus image recognition illustrated according to an exemplary embodiment of the disclosure.

FIG. 3 is a schematic diagram of a diabetic fundus image recognition illustrated according to an exemplary embodiment of the disclosure.

Referring to FIG. 3, in this exemplary embodiment, the user (e.g., a doctor) can transmit the diabetic fundus image (i.e., the image to be recognized) of a patient to the device 2000 of labeling feature through the input/output device 130. For example, the central processing unit 100 inputs a diabetic fundus image P1 to a neural network image recognition model 300, and outputs a determination result (e.g., the second level C2 of the diabetic lesion), an activation map AM0 corresponding to the zeroth level C0 of the diabetic lesion, an activation map AM1 corresponding to the first level C1 of the diabetic lesion, an activation map AM2 corresponding to the second level C2 of the diabetic lesion, an activation map AM3 corresponding to the third level C3 of the diabetic lesion, and an activation map AM4 corresponding to the fourth level C4 of the diabetic lesion. Here, a value of each pixel in the activation map is quantified by a grayscale value, wherein a larger value indicates that the pixel is more likely to be activated by the neural network image recognition model 300.

Figure 4:
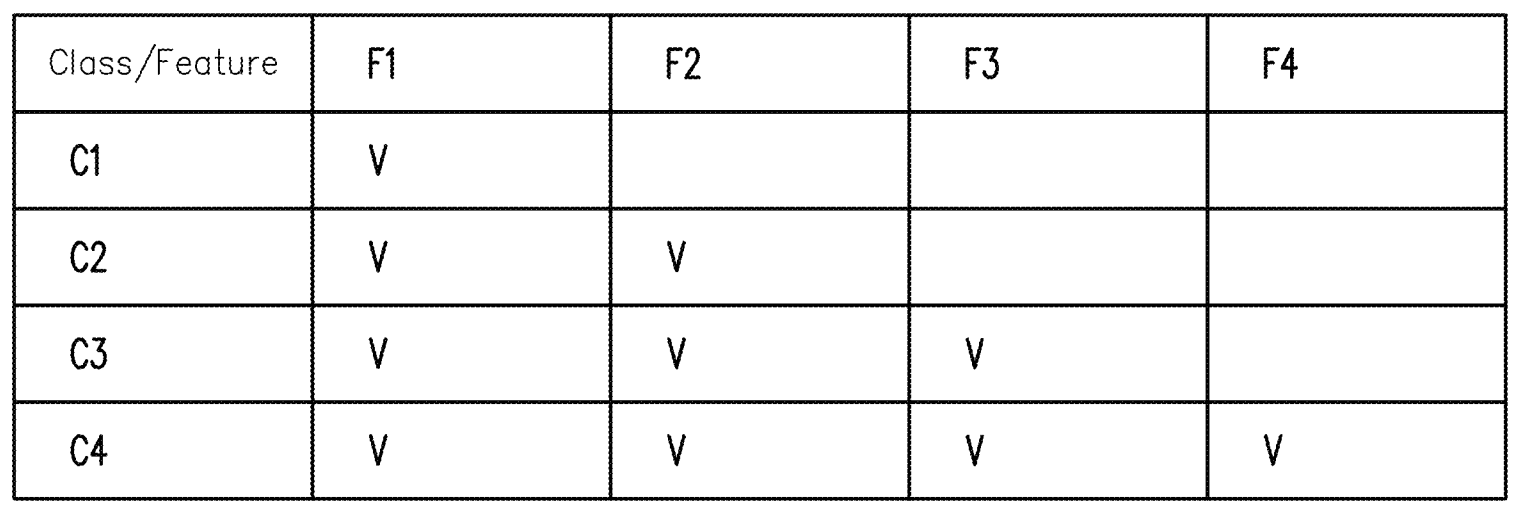

FIG. 4 is a diagram illustrating a relationship between diabetic lesion severity classes and preset features.

Referring to FIG. 4, because the levels of the diabetic lesion are determined by the included preset feature, images of the activation maps of the zeroth level C0, the first level C1, the second level C2, the third level C3 and the fourth level C4 of the diabetic lesion may be expressed respectively by the following equations.

$$C1=\{F|F\in F1\}$$

$$C2=\{F|F\in F1,F2\}$$

$$C3=\{F|F\in F1,F2,F3\}$$

$$C4=\{F|F\in F1,F2,F3,F4\}$$

A first present feature F1, a second present feature F2, a third present feature F3 and a fourth present feature F4 of the diabetic lesion may be expressed by the following set operations.

$$F1=C1\cap C2\cap C3\cap C4$$

$$F2=C2\cap C3\cap C4$$

$$F3=C3\cap C4$$

$$F4=C4-C3 \text{ or } C4\backslash C3$$

In this exemplary embodiment, after the activation map AM1 corresponding to the first level C1 of the diabetic lesion, the activation map AM2 corresponding to the second level C2 of the diabetic lesion, the activation map AM3 corresponding to the third level C3 of the diabetic lesion and the activation map AM4 corresponding to the fourth level C4 of the diabetic lesion are obtained, the central processing unit 100 performs a feature set operation to obtain a grayscale value matrix of a recognized feature corresponding to the preset feature from the activation maps. For example, based on the preset feature, the central processing unit 100 divides the activation maps into a feature map set containing the preset feature and a non-feature map set not containing the preset feature, and generates the grayscale value matrix for each of the activation maps to perform the feature set operation. Calculation of the grayscale value matrix of the recognized feature corresponding to the preset feature is described below with reference to FIG. 5 to FIG. 8.

Figure 5:
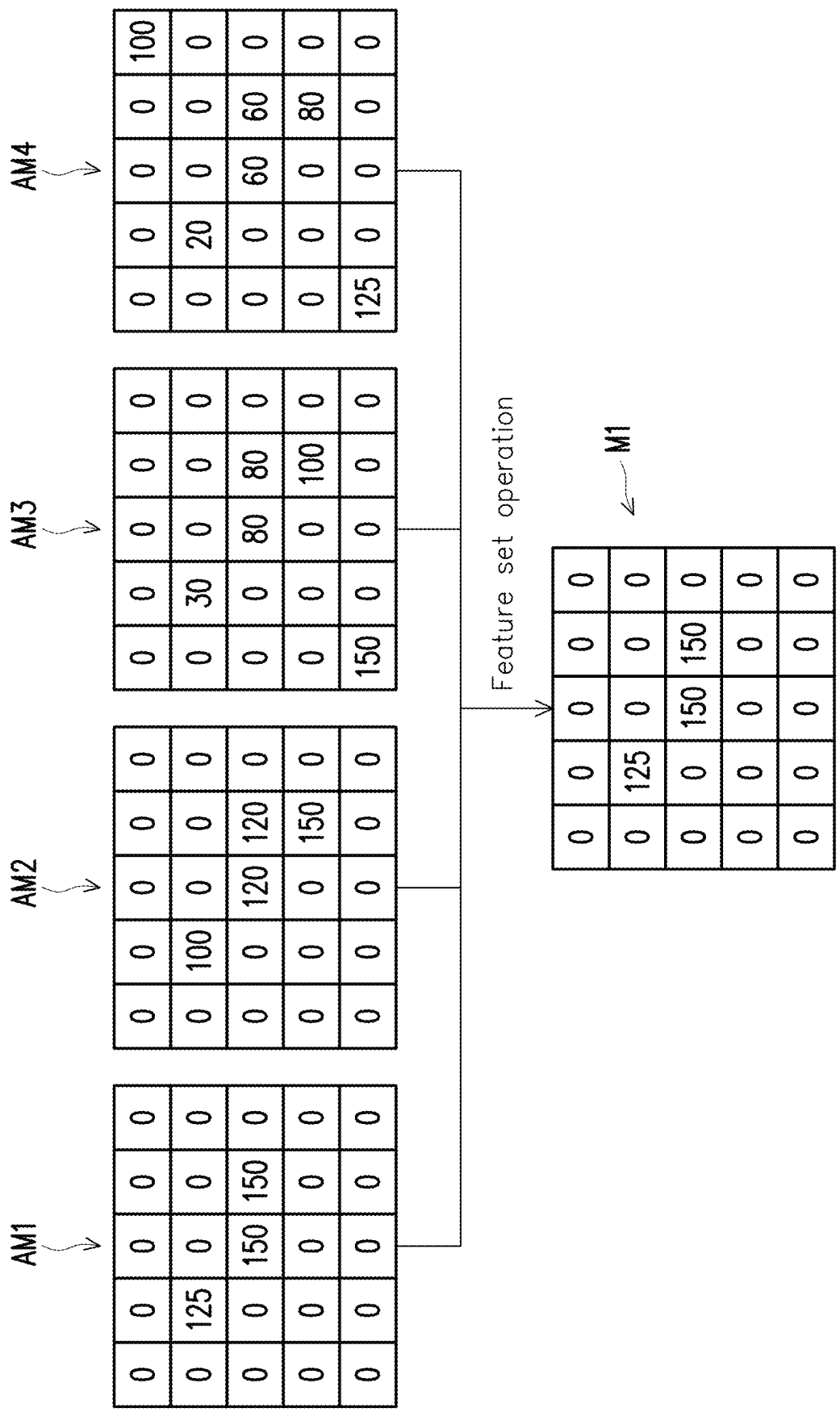
FIG. 5 is a schematic diagram illustrating a grayscale value matrix of a recognized feature corresponding to a first preset feature calculated from the activation maps.

FIG. 5 is a schematic diagram illustrating a grayscale value matrix of a recognized feature corresponding to a first preset feature calculated from the activation maps.

Referring to FIG. 5, as described above, the activation map AM1 corresponding to the first level C1 of the diabetic lesion, the activation map AM2 corresponding to the second level C2 of the diabetic lesion, the activation map AM3 corresponding to the third level C3 of the diabetic lesion and the activation map AM4 corresponding to the fourth level C4 of the diabetic lesion all belong to a feature map set containing the first preset feature. Accordingly, a grayscale value matrix M1 of the recognized feature corresponding to the first preset feature may be obtained by performing an intersection operation on the activation map AM1 corresponding to the first level C1 of the diabetic lesion, the activation map AM2 corresponding to the second level C2 of the diabetic lesion, the activation map AM3 corresponding to the third level C3 of the diabetic lesion and the activation map AM4 corresponding to the fourth level C4 of the diabetic lesion.

Figure 6:
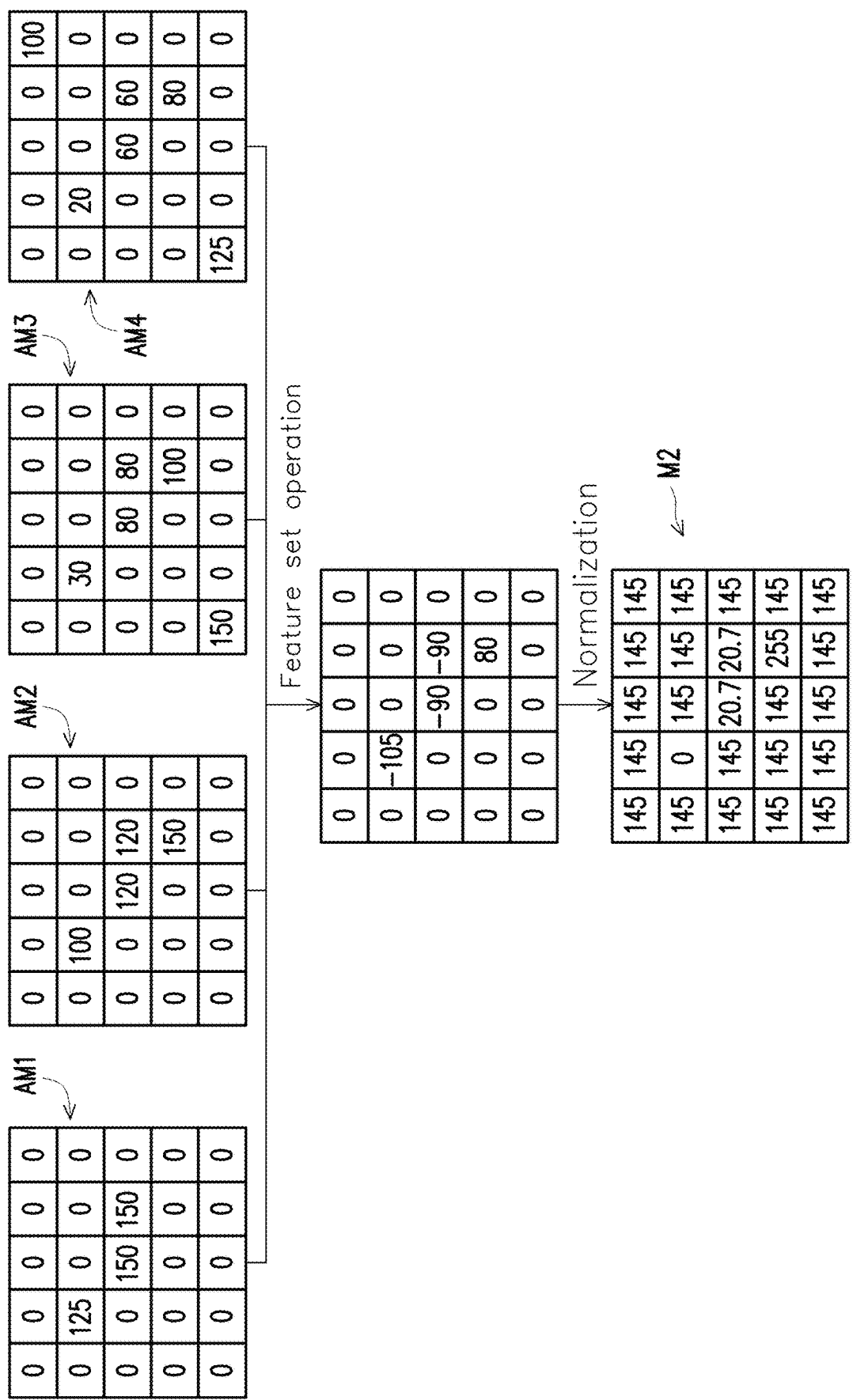
FIG. 6 is a schematic diagram illustrating a grayscale value matrix of a recognized feature corresponding to a second preset feature calculated from the activation maps.

FIG. 6 is a schematic diagram illustrating a grayscale value matrix of a recognized feature corresponding to a second preset feature calculated from the activation maps.

Referring to FIG. 6, as described above, the recognized feature corresponding to the second preset feature is present in the activation map AM2 corresponding to the second level C2 of the diabetic lesion, the activation map AM3 corresponding to the third level C3 of the diabetic lesion and the activation map AM4 corresponding to the fourth level C4 of the diabetic lesion, and is absent in the activation map AM1 corresponding to the first level C1 of the diabetic lesion. In other words, the activation map AM2 corresponding to the second level C2 of the diabetic lesion, the activation map AM3 corresponding to the third level C3 of the diabetic lesion and the activation map AM4 corresponding to the fourth level C4 of the diabetic lesion belong to a feature map set containing the second preset feature, and the activation map AM1 corresponding to the first level C1 of the diabetic lesion belongs to a feature map set not containing the second preset feature. Accordingly, the central processing unit 100 respectively obtains smallest grayscale values for corresponding positions from the activation map AM2 corresponding to the second level C2 of the diabetic lesion, the activation map AM3 corresponding to the third level C3 of the diabetic lesion and the activation map AM4 corresponding to the fourth level C4 of the diabetic lesion, respectively subtracts grayscale values of corresponding positions of the activation map AM1 corresponding to the first level C1 of the diabetic lesion from the obtained smallest grayscale values for each corresponding position, and perform a normalization, so as to form a grayscale value matrix M2 of the recognized feature corresponding to the second preset feature.

Figure 7:
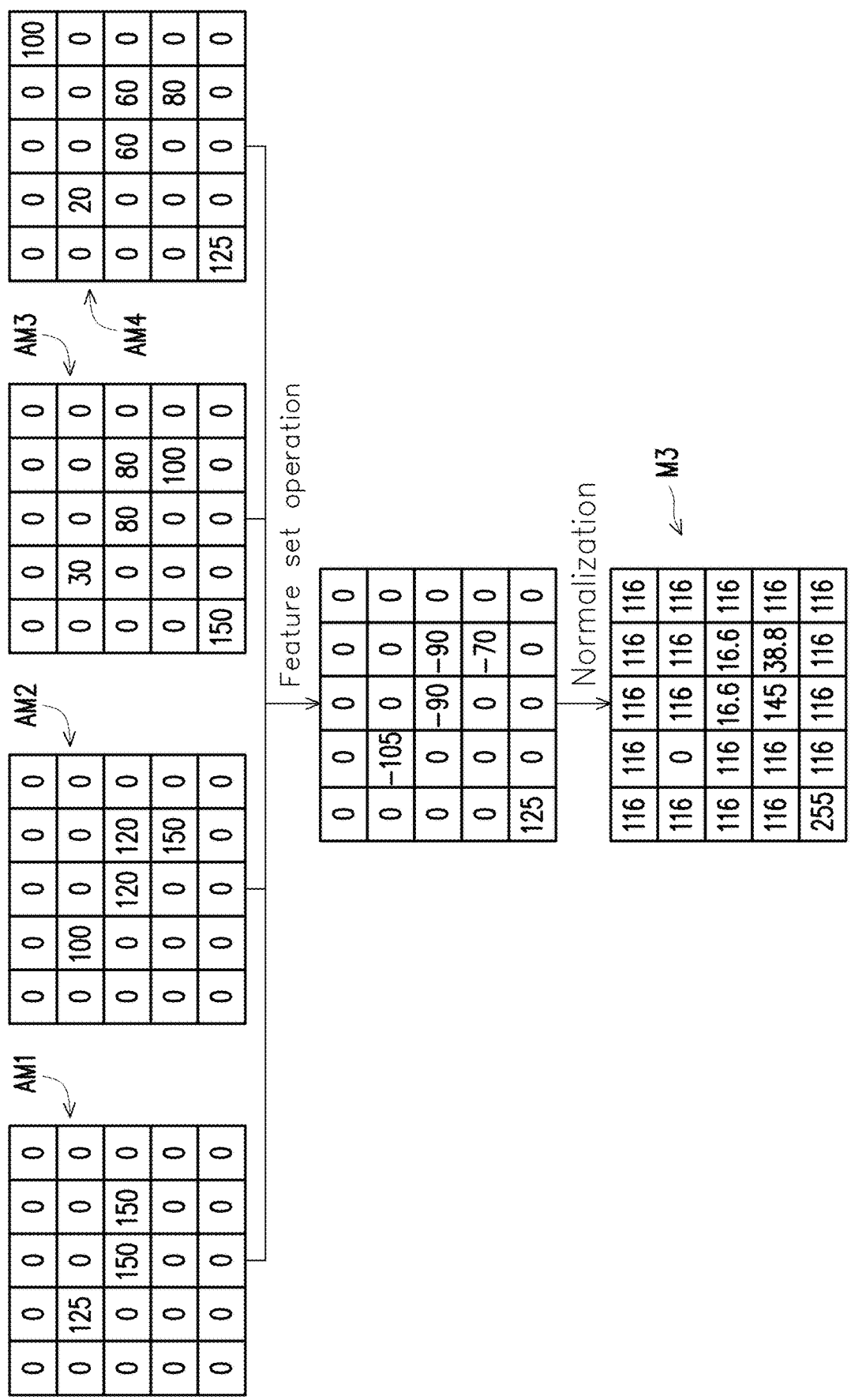
FIG. 7 is a schematic diagram illustrating a grayscale value matrix of a recognized feature corresponding to a third preset feature calculated from the activation maps.

FIG. 7 is a schematic diagram illustrating a grayscale value matrix of a recognized feature corresponding to a third preset feature calculated from the activation maps.

Referring to FIG. 7, as described above, the recognized feature corresponding to the third preset feature is present in the activation map AM3 corresponding to the third level C3 of the diabetic lesion and the activation map AM4 corresponding to the fourth level C4 of the diabetic lesion, and is absent in the activation map AM1 corresponding to the first level C1 of the diabetic lesion and the activation map AM2 corresponding to the second level C2 of the diabetic lesion. In other words, the activation map AM3 corresponding to the third level C3 of the diabetic lesion and the activation map AM4 corresponding to the fourth level C4 of the diabetic lesion belong to a feature map set containing the third preset feature, and the activation map AM1 corresponding to the first level C1 of the diabetic lesion and the activation map AM2 corresponding to the second level C2 of the diabetic lesion belong to a feature map set not containing the third preset feature. Accordingly, the central processing unit 100 obtains smallest grayscale values for each corresponding position from the activation map AM3 corresponding to the third level C3 of the diabetic lesion and the activation map AM4 corresponding to the fourth level C4 of the diabetic lesion, respectively subtracts greatest grayscale values, which are obtained based on corresponding positions of the activation map AM1 corresponding to the first level C1 of the diabetic lesion and the activation map AM2 corresponding to the second level C2 of the diabetic lesion, from the obtained smallest grayscale values for each corresponding position, and perform a normalization, so as to form a grayscale value matrix M3 of the recognized feature corresponding to the third preset feature.

Figure 8:
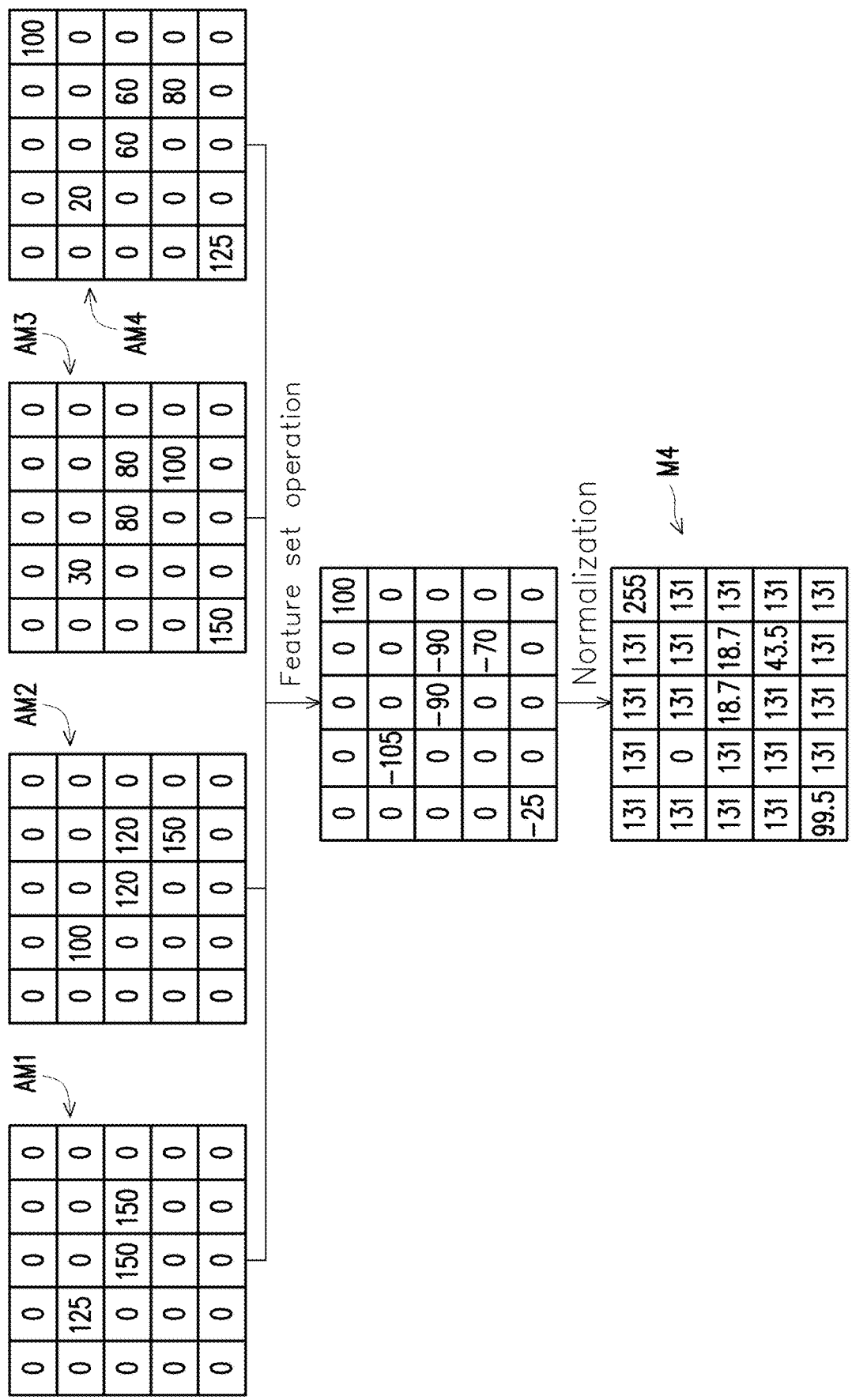
FIG. 8 is a schematic diagram illustrating a grayscale value matrix of a recognized feature corresponding to a fourth preset feature calculated from the activation maps.

FIG. 8 is a schematic diagram illustrating a grayscale value matrix of a recognized feature corresponding to a fourth preset feature calculated from the activation maps.

Referring to FIG. 8, as described above, the recognized feature corresponding to the fourth preset feature is present in the activation map AM4 corresponding to the fourth level C4 of the diabetic lesion, and is absent in the activation map AM1 corresponding to the first level C1 of the diabetic lesion, the activation map AM2 corresponding to the second level C2 of the diabetic lesion and the activation map AM3 corresponding to the third level C3 of the diabetic lesion. In other words, the activation map AM4 corresponding to the fourth level C4 of the diabetic lesion belongs to a feature map set containing the fourth preset feature, and the activation map AM1 corresponding to the first level C1 of the diabetic lesion, the activation map AM2 corresponding to the second level C2 of the diabetic lesion and the activation map AM3 corresponding to the third level C3 of the diabetic lesion belong to a feature map set not containing the fourth preset feature. Accordingly, the central processing unit 100 respectively obtains grayscale values for each corresponding position from the activation map AM4 corresponding to the fourth level C4 of the diabetic lesion, respectively subtracts greatest grayscale values, which are obtained based on corresponding positions of the activation map AM1 corresponding to the first level C1 of the diabetic lesion, the activation map AM2 corresponding to the second level C2 of the diabetic lesion and the activation map AM3 corresponding to the third level C3 of the diabetic lesion, from the grayscale values for each corresponding position, and perform a normalization, so as to form a grayscale value matrix M4 of the recognized feature corresponding to the fourth preset feature.

In this exemplary embodiment, the central processing unit 100 generates a feature mask corresponding to the recognized feature based on the grayscale value matrix of the recognized feature corresponding to the preset feature. For example, the central processing unit 100 generates a feature mask of the recognized feature corresponding to the first preset features based on the grayscale value matrix M1; generates a feature mask of the recognized feature corresponding to the second preset features based on the grayscale value matrix M2; generates a feature mask of the recognized feature corresponding to the third preset features based on the grayscale value matrix M3; generates a feature mask of the recognized feature corresponding to the fourth preset features based on the grayscale value matrix M4. In addition, the central processing unit 100 superimposes these feature masks with the diabetic fundus image P1 to be recognized and displays it through the input/output device 130, so as to label the recognized features on which the neural network image recognition model 300 is based. Accordingly, the user (the doctor) can confirm the recognized features and their positions in the diabetic fundus image to be recognized based on the superimposed image, and accordingly verify a determination result of the neural network image recognition model 300.

In particular, after the input/output device 130 labels the recognized features and their positions, the central processing unit 100 can further separate at least one other recognized feature and a position of the at least one other recognized feature from positions not labeled in the diabetic fundus image P1 to be recognized.

Figure 9:
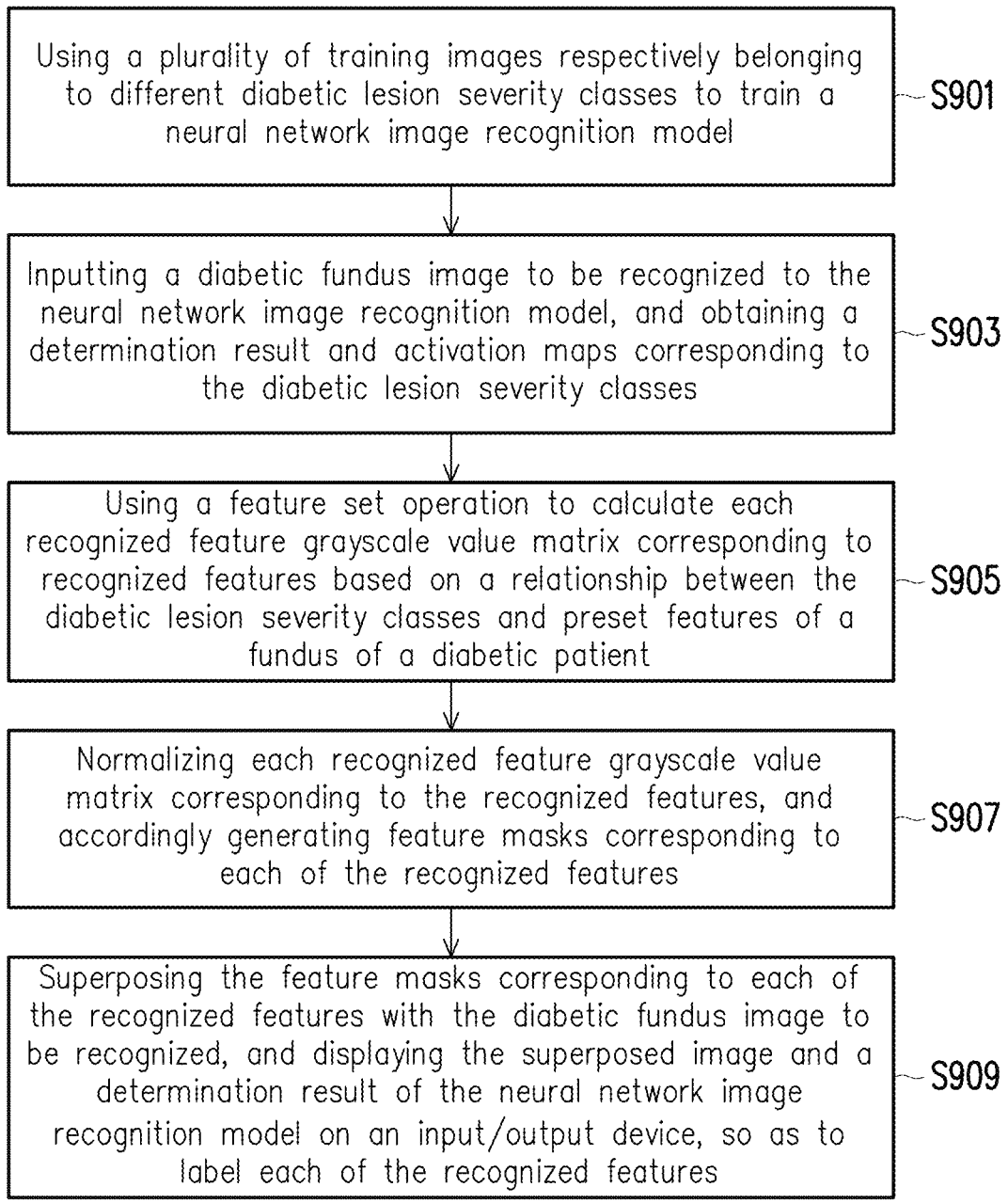
FIG. 9 is a flowchart of an apparatus of labelling features for image recognition illustrated according to an exemplary embodiment of the disclosure.

FIG. 9 is a flowchart of a method of labelling features for diabetic fundus image recognition illustrated according to an exemplary embodiment of the disclosure.

Referring to FIG. 9, in step S901, the central processing unit 100 uses a plurality of training images respectively belonging to different diabetic lesion severity classes to train a neural network image recognition model.

In step S903, the central processing unit 100 inputs a diabetic fundus image to be recognized to the neural network image recognition model, and obtains a determination result and activation maps respectively corresponding to the diabetic lesion severity classes.

In step S905, the central processing unit 100 uses a feature set operation to calculate each recognized feature grayscale value matrix corresponding to recognized features based on a relationship between the diabetic lesion severity classes and preset features of a fundus of a diabetic patient.

In step S907, the central processing unit 100 normalizes each recognized feature grayscale value matrix corresponding to the recognized features, and accordingly generates feature masks respectively corresponding to the recognized features.

In step S909, the central processing unit 100 superposes the feature masks respectively corresponding to the recognized features with the diabetic fundus image to be recognized, and displays the superposed image and a determination result of the neural network image recognition model on the input/output device 130, so as to label each of the recognized features.

In summary, according to the method and the apparatus of labelling features for image recognition in the exemplary embodiment of the disclosure, the recognized features in the image are extracted based on the relationship between the features and the classes. Accordingly, the method and the apparatus of labelling features for image recognition of the disclosure can display key features that activate this classification result from an output result of an artificial intelligence classification engine, and provide a mechanism for the user to find other hidden features.

The invention claimed is:

1. A method of labelling features for image recognition, comprising:
    inputting an image to be recognized to a neural network image recognition model to obtain a classification result, wherein the neural network image recognition model classifies the image to be recognized to one of a plurality of classes, the classes are created based on a plurality of preset features, and the classification result comprises a plurality of activation maps respectively corresponding to the classes;
    obtaining a plurality of recognized features activating the classification result and positions of the recognized features from the image to be recognized based on the activation maps respectively corresponding to the classes, wherein the recognized features are separately corresponding to one of the preset features; and labelling the recognized features activating the classification result and the positions of the recognized features,
   wherein the step of obtaining the recognized features activating the classification result and the positions of the recognized features from the image to be recognized based on the activation maps respectively corresponding to the classes comprises:
   extracting the recognized features by using a set operation based on a relationship between the preset features and the classes and the activation maps respectively corresponding to the classes.

2. The method of labelling features for image recognition according to claim 1, wherein the step of extracting the recognized features by using the set operation based on the relationship between the preset features and the classes and the activation maps respectively corresponding to the classes comprises:
   outputting a grayscale value matrix for each of the activation maps;
   grouping the activation maps respectively corresponding to the classes into a feature map set and a non-feature map set, wherein a first preset feature among the preset features is present in the activation map belonging to the feature map set among the activation maps and the first preset feature is absent in the activation map belonging to the non-feature map set among the activation maps based on the relationship between the preset feature and the classes; and
   respectively subtracting greatest grayscale values, which are obtained from each corresponding position of the grayscale value matrix of the activation map belonging to the feature map set, from smallest grayscale values obtained from each corresponding position of the grayscale value matrix of the activation map belonging to the non-feature map set, so as to generate a first recognized feature grayscale value matrix corresponding to the first preset feature.

3. The method of labelling features for image recognition according to claim 2, wherein the step of extracting the recognized features belonging to the preset features among the recognized features by using the set operation based on the relationship between the preset features and the classes and the activation maps respectively corresponding to the classes further comprises:
   recognizing the recognized feature belonging to the first preset feature among the recognized features and the position of the recognized feature belonging to the first preset feature based on the first recognized feature grayscale value matrix corresponding to the first preset feature.

4. The method of labelling features for image recognition according to claim 1, wherein the step of labelling the recognized features and the positions of the recognized features activating the classification result comprises:
   generating a plurality of feature masks corresponding to the recognized features respectively based on the obtained recognized features and the positions of the recognized features; and
   superposing the feature masks separately with the image to be recognized to label the recognized features on the image to be recognized.

5. The method of labelling features for image recognition according to claim 1, further comprising:
   obtaining at least one other recognized feature activating the classification result and a position of the at least one other recognized feature from the image to be recognized based on the activation maps respectively corresponding to the classes.

6. The method of labelling features for image recognition according to claim 1, further comprising:
   training the neural network image recognition model based on a plurality of training images respectively belonging to the classes.

7. An apparatus of labelling features for image recognition, comprising:
   a central processing unit, configured to input an image to be recognized to a neural network image recognition model to obtain a classification result, wherein the neural network image recognition model classifies the image to be recognized to one of a plurality of classes, the classes are created based on a plurality of preset features, and the classification result comprises a plurality of activation maps respectively corresponding to the classes;
   a storage device, coupled to the central processing unit, and configured to store the neural network image recognition model and the classification result;
   an input/output device, coupled to the central processing unit,
   wherein the central processing unit is further configured to obtain a plurality of recognized features activating the classification result and positions of the recognized features from the image to be recognized based on the activation maps respectively corresponding to the classes, wherein the recognized features are separately corresponding to one of the preset features,
   wherein the input/output device is configured to display the recognized features activating the classification result and the positions of the recognized features,
   wherein the central processing unit extracts the recognized features by using a set operation based on a relationship between the preset features and the classes and the activation maps respectively corresponding to the classes.

8. The apparatus of labelling features for image recognition according to claim 7, wherein the central processing unit outputs a grayscale value matrix for each of the activation maps, and groups the activation maps respectively corresponding to the classes into a feature map set and a non-feature map set, wherein a first preset feature among the preset features is present in the activation map belonging to the feature map set among the activation maps and the first preset feature is absent in the activation map belonging to the non-feature map set among the activation maps based on the relationship between the preset feature and the classes, and
   the central processing unit respectively subtracts greatest grayscale values, which are obtained from each corresponding position of the grayscale value matrix of the activation map belonging to the feature map set, from smallest grayscale values obtained from each corresponding position of the grayscale value matrix of the activation map belonging to the non-feature map set, so as to generate a first recognized feature grayscale value matrix corresponding to the first preset feature.

9. The apparatus of labelling features for image recognition according to claim 8, wherein the central processing unit recognizes the recognized feature belonging to the first preset feature among the recognized features and the position of the recognized feature belonging to the first preset feature based on the first recognized feature grayscale value matrix corresponding to the first preset feature.

10. The apparatus of labelling features for image recognition according to claim 7, wherein the central processing unit generates a plurality of feature masks corresponding to the recognized features respectively based on the obtained recognized features and the positions of the recognized features, superposes the feature masks separately with the image to be recognized, and displays the image to be recognized superposed with the feature masks on the input/output device so as to label the recognized features.

11. The apparatus of labelling features for image recognition according to claim 7, wherein the central processing unit is further configured to obtain at least one other recognized feature activating the classification result and a position of the at least one other recognized feature from the image to be recognized based on the activation maps respectively corresponding to the classes.

12. The apparatus of labelling features for image recognition according to claim 7, wherein the central processing unit is further configured to train the neural network image recognition model based on a plurality of training images respectively belonging to the classes.

* * * * *